United States Patent [19]

Fan et al.

[11] Patent Number: 5,096,837

[45] Date of Patent: Mar. 17, 1992

[54] IMMUNOCHROMATOGRAPHIC ASSAY AND METHOD OF USING SAME

[75] Inventors: Eugene Fan, La Jolla; Dou-Mei Wang, Encinitas; Fon-Chiu M. Chen, Ramona; Gregg L. Wilson, San Diego; Michael W. Milner, Murrieta; Ching Huang, Chula Vista, all of Calif.

[73] Assignee: Pacific Biotech, Inc., San Diego, Calif.

[21] Appl. No.: 476,788

[22] Filed: Feb. 8, 1990

[51] Int. Cl.⁵ .................. G01N 33/558; G01N 33/53; G01N 33/543; C12Q 1/00

[52] U.S. Cl. .................................... 436/514; 435/7.1; 435/962; 436/501; 436/533; 436/518; 436/814

[58] Field of Search .................. 435/4, 7, 7.1, 962; 436/513, 828, 518, 524, 811, 514, 501, 533, 814

[56] References Cited

U.S. PATENT DOCUMENTS

| | | |
|---|---|---|
| 4,169,138 | 9/1979 | Jonsson . |
| 4,181,636 | 1/1980 | Fisher ................................ 435/7 |
| 4,373,932 | 2/1983 | Gribnau et al. . |
| 4,376,110 | 3/1983 | David et al. . |
| 4,419,435 | 12/1983 | Dorman et al. .............. 436/534 |
| 4,496,654 | 1/1985 | Katz et al. . |
| 4,552,839 | 11/1985 | Gould et al. . |
| 4,591,570 | 5/1986 | Chang . |
| 4,632,901 | 12/1986 | Valkirs et al. . |
| 4,680,274 | 7/1987 | Sakai et al. .................. 436/578 |
| 4,703,017 | 10/1987 | Campbell et al. . |
| 4,855,240 | 8/1989 | Rosenstein et al. . |
| 4,912,034 | 3/1990 | Kalra et al. . |

FOREIGN PATENT DOCUMENTS

| | | |
|---|---|---|
| 0323605 | 12/1988 | European Pat. Off. . |
| 8001515 | 1/1980 | PCT Int'l Appl. . |
| 8808534 | 4/1988 | PCT Int'l Appl. . |
| 2204398 | 4/1988 | United Kingdom . |

OTHER PUBLICATIONS

Johnstone et al., Immunochemistry in Practice, Blackwell Sci. Pub. Boston 1987.

Bangs, L. B., "Uniform Latex Particles," 41st National Meeting, American Association for Clinical Chemistry, 1989, Seragen Diagnostics Inc., Indianapolis, IN.

Galloway, R. J., "Development of microparticle tests and immunoassays," ©1988 by Seradyn, Inc., Indianapolis, IN.

Manual of Clinical Microbiology, 4th Ed., American Society for Microbiology, pp. 170–171.

Primary Examiner—Robert A. Wax
Assistant Examiner—D. R. Preston
Attorney, Agent, or Firm—Knobbe, Martens, Olson & Bear

[57] ABSTRACT

The invention disclosed herein relates to the field of one-step assays and latex agglutination tests ("LAT"), and provides an improved method of preparing and using a one-step immunoassay, as well as improved methods of preparing coated latex particles for use in diagnostic assays, and especially, immunochromatographic assays.

15 Claims, 3 Drawing Sheets

FIG. 1

| STREP A. | | A. STREP A. Ab/LATEX ONLY | | B. MIXTURE OF STREP A.Ab/L+BSA/L | |
|---|---|---|---|---|---|
| CELLS PER TEST | TEST TIME | Ab/LATEX CONC. 3% | Ab/LATEX CONC. 1% | (STREP A/L) 1% | + (BSA/L) 2% |
| $5 \times 10^9$ | 3 min | | | | |
| " | 10 min | | | | |
| $5 \times 10^8$ | 3 min | | | | |
| " | 10 min | | | | |
| $1 \times 10^5$ | 3 min | | | | |
| " | 10 min | | | | |

LOW DOSE OF STREP A

FIG. 2

| STREP A. Ag PER TEST | RUN TIME | A. STREP A. Ab/LATEX (1%) + PLAIN LATEX (2%) | B. MIXTURE OF STREP A. Ab /LATEX (1%) + BSA/LATEX (2%) | REMARK |
|---|---|---|---|---|
| $5 \times 10^9$ CELLS | 3 min | | | B. MOVED FASTER AND SHOWED SIGNAL |
| " | 10 min | | | B. BACKGROUND IS BETTER |
| $5 \times 10^8$ CELLS | 3 min | | | A & B: MOVED EQUALLY |
| " | 10 min | | | B: BACKGROUND IS BETTER |
| $1 \times 10^5$ CELLS | 3 min | | | A = B |
| " | 10 min | | | A = B |

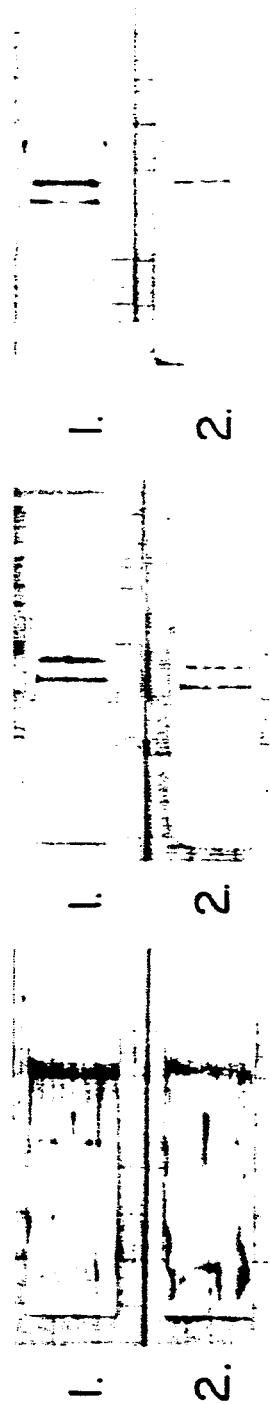

IMMUNOCHROMATOGRAPHIC ASSAY AND METHOD OF USING SAME

BACKGROUND OF THE INVENTION

Uniform latex particles ("ULPs") are, in general, extremely uniform spheres of small diameter. Typical diameters range from less than about 0.1 $\mu$m to about 100 $\mu$m. Particles smaller than 5 $\mu$m are usually prepared by emulsion polymerization. The result of this process is a series of particles with extremely uniform size distributions.

The principal use for ULPs is in the medical diagnostic area, wherein the particles are utilized for latex agglutination tests. Newer suggested uses include microbiological applications—e.g., bacterial typing and identification, and measurement of serum blood levels of antibiotics. (See, e.g., Bangs, L.B., "Uniform Latex Particles," presented at a workshop at the 41st National Meeting, American Association for Clinical Chemistry, 1989, and available in printed form from Seragen Diagnostics Inc., Indianapolis, IN; or Galloway, R.J., "Development of microparticle tests and immunoassays," ©1988 by Seradyn, Inc., Indianapolis, IN.) Other varieties of particles, such as amide-modified latex ("AML") and carboxylate-modified latex ("CML") have amide and carboxylic acid groups, respectively, on their surfaces. These functional groups permit covalent binding of antigens or antibodies to the surface of the ULPs for improved agglutination tests.

The largest use of ULPs is in the field of immunodiagnostics or immunoassays, especially in latex agglutination tests, where they are used to detect the presence of very minute amounts or concentrations or antigens or antibodies, in the blood, serum, urine, or cerebrospinal fluid. In essence, ULPs are used to magnify or visualize the antigen/antibody complex formation; they can also be used to quantify this reaction.

For example, if one is attempting to measure a particular antibody ("Ab"), an appropriate antigen ("Ag") is coated onto the latex particles. Since the Ab is divalent, it may bind to identical sites on two adjacent particles and link them together. Thus, if Ab present in an individual's sample is mixed with the Ag-coated particles, it will cause agglutination or coagulation of the particles; these aggregates are generally visible to the naked eye. This phenomenon is, essentially, the basis for latex agglutination tests ("LAT").

One major difficulty with LATs is the fact that the coated particles tend to spontaneously agglutinate. This is largely due to the fact that latex suspensions are colloidal suspensions of hydrophobic particles. The stability of the suspension is dependent upon the surface active charges; addition of small amounts of protein (approximately 10 $\mu$g per mg of latex) can cause agglomeration, whereas continued addition of larger amounts of protein tends to increase particle stability.

This type of agglutination is also a problem in the chromatographic assays using colored or visible particles, such as the assay disclosed in published PCT Application No. WO88/08534. In this assay, a sample is applied to a substrate of absorbent material, and analyte binds to antibody or antigen bearing, mobile colored latex particles. The particles to which analyte binds are themselves bound by immobilized immunoreagent as the sample chromatographically traverses the length of the absorbent material.

Various methods of addressing this problem and the related problem of nonspecific agglutination have been suggested, including the use of linkers and spacers. Some of the suggested spacers include Protein A, diaminoalkanes, naked antibodies, and streptavidin-biotin spacers, to name a few. The use of heterobifunctional linkers, halogen substituted carboxylic acids, bovine serum albumin, surfactants, and F(ab)$_2$ fragments has also been suggested. However, few of these suggestions prove entirely satisfactory, as they tend to interfere with the assay, many doing so in a manner that inhibits agglutination. This is, of course, completely unacceptable for LATs.

Therefore, in response to an express need for an immunoassay procedure with diverse applicability, which avoids the agglomeration problems of other assays and which promotes the goals of improved accuracy and greater resolution, and which is also elegant in its simplicity, the Applicants hereby disclose the present invention, including its equivalents thereof.

SUMMARY OF THE INVENTION

According to one aspect of the present invention, there is provided, in an immunoassay involving the interaction of an antibody and an antigen, wherein one of the reagents used in the assay comprises a first mobile polymer particle to which antibody or antigen is bound, the improvement comprising providing the first particle in an admixture with a second mobile polymer particle to which a protein is bound, wherein the protein does not participate in the antibody-antigen interaction. In an alternative embodiment, the invention further comprises applying the admixture to a portion of a support layer. Another variation provides for immobilizing the admixture onto a first defined zone of a support layer having one or more defined zones.

In a preferred embodiment, the immunoassay further comprises immobilizing anti-rabbit immunoglobulin G (IgG) onto a second defined zone of the support layer. In another variation, the protein bound to the second mobile particle is BSA. In an alternative embodiment, the mobile particles are from about 0.1 $\mu$ to about 0.8 $\mu$ in diameter. In a preferred embodiment, the mobile particles are colored. Yet another embodiment provides for the addition of an agent to prevent nonspecific binding, together with a detergent, to the admixture.

Another aspect of the present invention discloses a method of reducing or eliminating false positive and/or false negative reactions from immunoassays, particularly when ligand-bound particles are mixed with BSA-bound particles.

In a preferred embodiment, the mobile polymer particles comprise a mixture of particles to which ligand is bound, and particles to which ligand is not bound. According to yet another embodiment, the particles to which ligand is not bound are coated with a protein that does not participate in the ligand-antiligand binding used in the assay, such as BSA. In yet another embodiment, the polymer particles comprise latex or polystyrene beads.

Any of the above-noted embodiments may also be incorporated into a kit. Such a kit may further comprise reagents, vials, agent to prevent nonspecific binding, and instructions for use; such kits may further comprise a filtering apparatus.

The invention also includes a support layer for performing an assay, in which polymer particles are provided, wherein some of the particles are labeled with an antibody or antigen, and an effective agglomeration-reducing amount of the particles are not labeled with that antigen or antibody.

Of course, the invention includes the method of performing the assay, the method for preventing agglomeration, and the particular unique reagents (or reagent mixtures) used in such assays, as well as devices or kits containing those materials.

BRIEF DESCRIPTION OF THE DRAWINGS

FIG. 1. diagrams the results of using an antibody-latex/BSA-latex mixture in a Strep A Test, test run No. 1.

FIG. 2 diagrams the results of using an antibody-latex/BSA-latex mixture in a Strep A Test, test run No. 2.

FIG. 3 diagrams the results of using an antibody-latex/BSA-latex mixture in an Occult Blood Test.

DETAILED DESCRIPTION

We have found that many immunoassays currently in use have impaired accuracy, due to the occurrence of false negatives and false positives. We believe that we have significantly reduced, if not eliminated, such problems.

A. Preparation of Antibody-Latex Conjugates

The basic process of protein-latex conjugation, either via simple adsorption or covalent binding, is well known in the art, as is the use of colored latex particles, which increase the resolution and readability of immunoassays. Various procedures are described, in general terms, in Bangs, L.B., "Uniform Latex Particles," presented at a workshop at the 41st National Meeting, Amer. Assoc. Clin. Chem., 1989, and available in printed form from Seragen Diagnostics Inc., Indianapolis, IN; or Galloway, R.J., "Development of microparticle tests and immunoassays," Seradyn, Inc., Indianapolis, IN. These articles, and references cited to therein, are hereby incorporated by reference.

One method of preparing coated ULPs is the adsorption method. In general terms, one should: 1) utilize pure reagents; 2) clean the particles prior to coating; and 3) determine the quantitative surface coverage of the ULP and the ligand chemistry. For example, antibody-latex conjugates ("Ab-latex") may be prepared according to the following method: in the simplest case, the appropriate ligand is dissolved in a buffer solution, added to a latex suspension, and stirred for times ranging from a few minutes to more than 24 hours. After equilibration, the latex is centrifuged and the supernatant containing any unadsorbed ligand is discarded. The latex is re-suspended in fresh buffer and centrifuged; the supernatant is again discarded. Repeat these steps until the latex is adjudged to be washed free of any residual un-adsorbed ligand. At this juncture, the latex coating process may be complete and the latex ready to use in LATs.

Covalent coupling involves the permanent or covalent binding of a ligand or other material to the latex particle surface. If covalent coupling is the method of choice, one must first couple the ligand to the ULPs, then maintain the stability of the latex particle suspension, followed by preventing the protein from becoming denatured. (For a general discussion of covalent coupling techniques, and citation to more detailed references, see Bangs, L.B., "Uniform Latex Particles," which has been incorporated herein by reference.)

While the foregoing discussion is in the context of latex particles, it will be appreciated that other polymer particles, such as polystyrene particles, and even metal particles, such as gold sol particles, may be used. These particles and their methods of preparation are well known.

B. Preparation of BSA-Latex Conjugates

Preparation of bovine serum albumin - latex conjugates ("BSA-latex") is similar to Ab-latex preparation, as described above, except that no antibody is used in the preparation, and BSA is used instead. Alternatively, other proteins may be used in place of the BSA, such as other albumins (including lactalbumin), casein, globulin, immunoglobulin (which does not participate in the antigen-antibody reaction), and the like that can prevent nonspecific binding.

C. Mixture of Ab-latex and BSA-latex

Ab-latex and BSA-latex are mixed together in varying ratios, depending upon the test to be performed. For example, in preparing mixtures for use as set out in the Examples below, Ab-latex and BSA-latex were mixed in approximately a 1:1 ratio and a 1:3 ratio, volume to volume, for use in the Occult Blood Test (see Example II). In the Strep A Test (Example I), the ratio was approximately 1:2, Ab-latex:BSA-latex. Of course, the ratios can vary substantially, with greater amounts of protein-labeled latex resulting in greater reduction of nonspecific binding. The amount of latex (or other particle) that does not have antibody on can be any amount that is effective to appreciably decrease nonspecific binding, or false positives. Such amounts are readily determined by obvious empirical methods.

D. One-Step Assay Procedure

The assay reaction unit utilized in one particular embodiment of the invention has a strip of nitrocellulose membrane with a pore size of about 8 $\mu$, albeit larger or smaller pore sizes may be utilized (i.e., preferably in a range of about 3 $\mu$ to about 12 $\mu$). The strip is housed in a plastic casing. It is important to note the relationship of pore size and particle size; the diameter of the particles used should be smaller than the pore size of the membrane, so that the particles can move through the membrane.

Approximately 5 $\mu$l each of Ab-latex or Ab-latex/BSA-latex mixture ("Ab/BSA") was applied to the membrane in a mobile manner, and specific Ab (positive signal) and goat anti-rabbit IgG (negative signal) were immobilized on the membrane prior to testing, in discrete zones. (The goat anti-rabbit IgG can be obtained from many sources, e.g., Pel-Freez, Rogers, AR.) These zones may, however, be contiguous or overlapping.

In the performance of the assay, a sample is applied to the membrane, and flows along the membrane due to capillary action. The flowing sample carries the latex mixture along the membrane, and analyte in the sample binds to the antibody-labeled latex. The latex that is bound to analyte becomes immobilized to the "positive signal" Ab, and the latex that only has rabbit Ab bound to it is immobilized to the "negative signal" Ab. When the labeled latex is colored, a visible signal is produced in the positive and negative zones.

The invention can be better understood by way of the following examples which are representative of the preferred embodiments thereof, but which are not to be construed as limiting the scope of the invention.

EXAMPLE I

Strep A Test

We prepared the carbohydrate antigen of Group A streptococcus (Strep A antigen) by the nitrous acid extraction method (Manual of Clinical Microbiology, 4th Ed., American Society for Microbiology). The Strep A antigen solution (0.25 ml) was transferred to the sample application site of an immunoassay device comprising, at a minimum, a support layer or membrane having one or more defined zones, with ligand or antiligand bound thereto, wherein the sample was placed on the support layer in a region outside the defined zones, and then a liquid flow was supplied to the support layer, thereby allowing the specimen to diffuse across the defined zones and allowing substances in the specimen to become bound thereto. At least one of the defined zones has colloidal particles having a ligand bound thereto, wherein the ligand and any analyte in the sample are both complementary to the antiligand bound in the first defined zone. (Immunoassay devices often surround or support the membrane with a plastic casing, as well.)

Two identical tests were run, side-by-side. One test was terminated at 3 minutes, the other at 10 minutes.

Using Ab-latex alone (see FIG. 1.A.), concentrations of antigen equivalent to between $2.5 \times 10^8$ and $2.5 \times 10^9$ Strep A cells per test caused the Ab-latex to agglutinate. As a result, only a very small amount of latex moved across the nitrocellulose membrane, causing the positive signals to be very faint at 3 and 10 minutes. On the other hand, when the Ab/BSA mixture was used (see FIG. 1.B.), the same number of Strep A cells per test that caused agglutination in the Ab-latex failed to cause as much agglutination in the Ab/BSA mixture. This was evidenced by the fact that more latex was seen travelling along the membrane when the Ab/BSA was used. With this higher volume of latex movement came a subsequent increase in signal strength at 3 and 10 minutes, when compared with the Ab-latex alone. However, at lower concentrations of Strep A cells ($5 \times 10^4$ cells per test), both the Ab-latex and the Ab/BSA mixture showed similar results in terms of amount of latex moving and signal strength.

Using a mixture of Ab-latex and plain latex (FIG. 2.A.), $2.5 \times 10^9$ Strep A cells per test caused some latex to agglutinate and the positive signal was not visible but the background was dark and uncleared when compared to Ab/BSA (FIG. 2.B.). At $2.5 \times 10^8$ cells or less per test (FIG. 2.B.), the Ab/BSA mixture showed a more clear background when compared to the test using a mixture of Ab-latex and plain latex (FIG. 2.A.). However, even the combination of Ab-latex and plain latex showed better latex movement than the Ab-latex alone (FIG. 1.A. and FIG. 2.A.).

EXAMPLE II

Occult Blood Test

Two sample sticks from an occult blood test kit (such as that disclosed in our pending U.S. Pat. Application Ser. No. 409,003) were smeared with a fecal sample and were put into an extraction cup containing 350 $\mu$l extraction solution containing 0.1% Triton in 50 mM Tris buffer, pH 8.0. (Tris and Triton obtained from Sigma Co., St. Louis, MO.) After 10 seconds of rapid movement in the extraction solution, the sample sticks were discarded and the extraction mixture was transferred to the sample application site of an immunoassay device, such as that described in Example I. The assay was terminated after 10 minutes by removing the membrane from its plastic casing.

Our observations were similar to those noted for the Strep A test. We found that in the presence of human hemoglobin (126 ng–600 ng per test) the Ab-latex tended to agglutinate much too early, giving an uneven latex movement ("streaking" appeared on the signal window; see FIG. 3). Because of this early agglutination, less latex was able to move across the signal window, and the signal appeared somewhat garbled and "unfinished". With the addition of BSA-latex, a more even movement of the latex was observed. The result of using an Ab/BSA mixture was a cleaner background and equal or better sensitivity than was achieved with Ab-latex alone. Comparing the mixture of Ab-latex and BSA-latex in a 1:1 ratio versus that of 1:2 or 1:3, the higher the BSA-latex concentration, the better the background and the faster the movement of the latex across the signal window (FIG. 3).

These results indicated that using a mixture of Ab-latex and BSA-latex, instead of Ab-latex alone, improved the performance of the test without compromising the test sensitivity. We have hypothesized that the BSA-latex in the Ab/BSA mixture might be functioning as a "spacer", thus preventing the immediate agglutination of the Ab-latex in the presence of the test antigen. We have further noted that the use of the Ab/BSA mixture tends to eliminate non-specific binding and false positives, as well.

EXAMPLE III

HCG-Urine Test

We have noted that the use of Ab/BSA mixture reduces or eliminates the occurrence of false positives in HCG urine one-step tests. When Ab-latex alone was applied to the support prior to running the test, it has been noted that a false positive may result; when the Ab/BSA latex mixture was used to test the same urine, no false positives were noted. The occurrence of false positives is likely with some urine specimens due to the presence of substances which will cause non-specific binding to Ab-latex and immobilized Ab, resulting in the formation of a "sandwich." The presence of BSA-latex may interfere with non-specific binding, thus reducing or eliminating the occurrence of false positives. The substances in urine which cause such non-specific binding are likely to be protein A from *Staphylococcus areus*. It is known that protein A from *S. areus* strongly binds IgG, and if S. areus are present in the uring of a non-pregnant woman, a false positive reaction may be seen.

Although the invention has been described in the context of particular embodiments, it is intended that the scope of coverage of the patent not be limited to those particular embodiments, but be determined by reference to the following claims.

We claim:

1. In an assay involving the interaction of antigens and antibodies, wherein one of the reagents used in the assay comprises a first mobile particle to which antigen or antibody is bound, the improvement comprising providing said first particle in admixture with a second mobile particle to which said antigen or antibody is not bound, or to which a molecule non-reactive with said antigen or antibody is bound, wherein said second particle is present in an amount effective to decrease nonspecific binding, wherein said assay includes a support layer on which antigen-antibody interaction takes place, and wherein said admixture is applied on said support layer.

2. The assay of claim 1, wherein said admixture is applied onto a first defined zone of said support layer.

3. The assay of claim 2, wherein a first antigen or antibody is bound to said first mobile particle and a second antigen or antibody is immobilized in a second defined zone of said support layer.

4. The assay of claim 3, wherein said first antigen or antibody comprises a first antibody against an analyte and wherein said second antigen or antibody comprises a second antibody against said analyte.

5. The assay of claim 3, wherein said first antigen or antibody comprises an antigen against an analyte, which analyte comprises an antibody, and wherein said second antigen or antibody comprises an anti-antibody.

6. The assay of claim 3, wherein said first antigen or antibody comprises an anti-antibody, wherein said analyte comprises an antibody, and wherein said second antigen or antibody comprises an antigen against said analyte.

7. The assay of claim 1, wherein said non-reactive molecule is a protein bound to said second mobile particle, wherein said protein does not participate in said antigen-antibody interaction.

8. The assay of claim 7, wherein said protein bound to said second mobile particle is albumin.

9. The assay of any one of claims 1, 3, 7, or 13, wherein said mobile particles are from about 0.1 $\mu$ to about 0.8 $\mu$ in diameter.

10. The assay of claim 8, wherein said protein is bovine serum albumin.

11. The assay of claim 7, wherein said protein is IgG.

12. The assay of claim 11 wherein said mobile particles are colored.

13. The assay of claim 1, wherein said first mobile particles comprise latex particles to which antigen or antibody is bound, and said second mobile particles comprise plain latex particles.

14. The assay of claim 1, wherein said admixture further comprises an agent to prevent nonspecific binding and a detergent.

15. A method for minimizing agglomeration of antibody labeled or antigen labeled particles used in an immunoassay, comprising the step of providing an effective agglomeration-reducing amount of a particle that is not labeled with said antibody or antigen in admixture with said labeled particles.

* * * * *